United States Patent
Kang et al.

(10) Patent No.: US 11,197,717 B2
(45) Date of Patent: Dec. 14, 2021

(54) OPTICAL IRRADIATION APPARATUS

(71) Applicants: PUKYONG NATIONAL UNIVERSITY INDUSTRY-UNIVERSITY COOPERATION FOUNDATION, Busan (KR); INHA UNIVERSITY RESEARCH AND BUSINESS FOUNDATION, Incheon (KR)

(72) Inventors: Hyun Wook Kang, Busan (KR); Don Haeng Lee, Seoul (KR); Seok Jeong, Seoul (KR)

(73) Assignees: PUKYONG NATIONAL UNIVERSITY INDUSTRY-UNIVERSITY COOPERATION FOUNDATION, Busan (KR); INHA UNIVERSITY RESEARCH AND BUSINESS FOUNDATION, Incheon (KR)

( * ) Notice: Subject to any disclaimer, the term of this patent is extended or adjusted under 35 U.S.C. 154(b) by 147 days.

(21) Appl. No.: 16/491,531

(22) PCT Filed: Oct. 31, 2018

(86) PCT No.: PCT/KR2018/013069
§ 371 (c)(1),
(2) Date: Sep. 5, 2019

(87) PCT Pub. No.: WO2019/225816
PCT Pub. Date: Nov. 28, 2019

(65) Prior Publication Data
US 2021/0153938 A1    May 27, 2021

(30) Foreign Application Priority Data
May 24, 2018   (KR) .......................... 10-2018-0059045

(51) Int. Cl.
A61B 18/24    (2006.01)
A61M 25/10    (2013.01)
(Continued)

(52) U.S. Cl.
CPC ......... *A61B 18/24* (2013.01); *A61M 25/1002* (2013.01); *A61B 2018/00577* (2013.01);
(Continued)

(58) Field of Classification Search
None
See application file for complete search history.

(56) References Cited

U.S. PATENT DOCUMENTS 4,406,656 A * 9/1983 Hattler .............. A61M 25/0009
                                                            604/103.14
5,139,494 A * 8/1992 Freiberg ................. A61B 18/24
                                                            606/3
(Continued)

FOREIGN PATENT DOCUMENTS

JP    H0724662 B2    3/1995
JP    5990460 B2     9/2016
(Continued)

*Primary Examiner* — Jenna Zhang

(57) ABSTRACT

The present invention provides an optical irradiation apparatus including: a dual laser light source unit which simultaneously or selectively outputs multiple light sources created with different outputs; an optical fiber which is connected to the dual laser light source unit, receives the light outputted from the dual laser light source unit, and emits the received light through an embossed end surface; and an inflatable balloon catheter which is formed to surround the embossed end surface of the optical fiber and expands constricted tissue. With the present invention, it is
(Continued)

possible to effectively treat constricted tissue during a procedure of performing an anticancer therapy on entire human bodies with various types of cancers, and it is possible to mitigate patient's pain by reducing a relapse rate of stenosis after the photothermal therapy.

6 Claims, 13 Drawing Sheets

(51) Int. Cl.
*A61B 90/00* (2016.01)
*A61B 18/00* (2006.01)
*A61B 18/22* (2006.01)

(52) U.S. Cl.
CPC .............. *A61B 2018/00589* (2013.01); *A61B 2018/2255* (2013.01); *A61B 2090/3966* (2016.02); *A61M 2025/105* (2013.01); *A61M 2025/1079* (2013.01)

(56) References Cited

U.S. PATENT DOCUMENTS

| | | | | |
|---|---|---|---|---|
| 5,395,332 | A * | 3/1995 | Ressemann | A61M 25/0068 600/585 |
| 2002/0052621 | A1* | 5/2002 | Fried | A61B 18/24 606/192 |
| 2005/0165462 | A1* | 7/2005 | Bays | A61N 5/0601 607/88 |
| 2007/0270717 | A1* | 11/2007 | Tang | G02B 6/262 600/585 |
| 2009/0270850 | A1* | 10/2009 | Zhou | A61B 18/24 606/15 |
| 2017/0050043 | A1* | 2/2017 | Kang | A61N 5/0603 |

FOREIGN PATENT DOCUMENTS

| | | |
|---|---|---|
| KR | 20110112269 A | 10/2011 |
| KR | 20110120920 A | 11/2011 |
| KR | 20150120781 A | 10/2015 |
| KR | 20160027441 A | 3/2016 |
| KR | 101784213 B1 | 10/2017 |

* cited by examiner

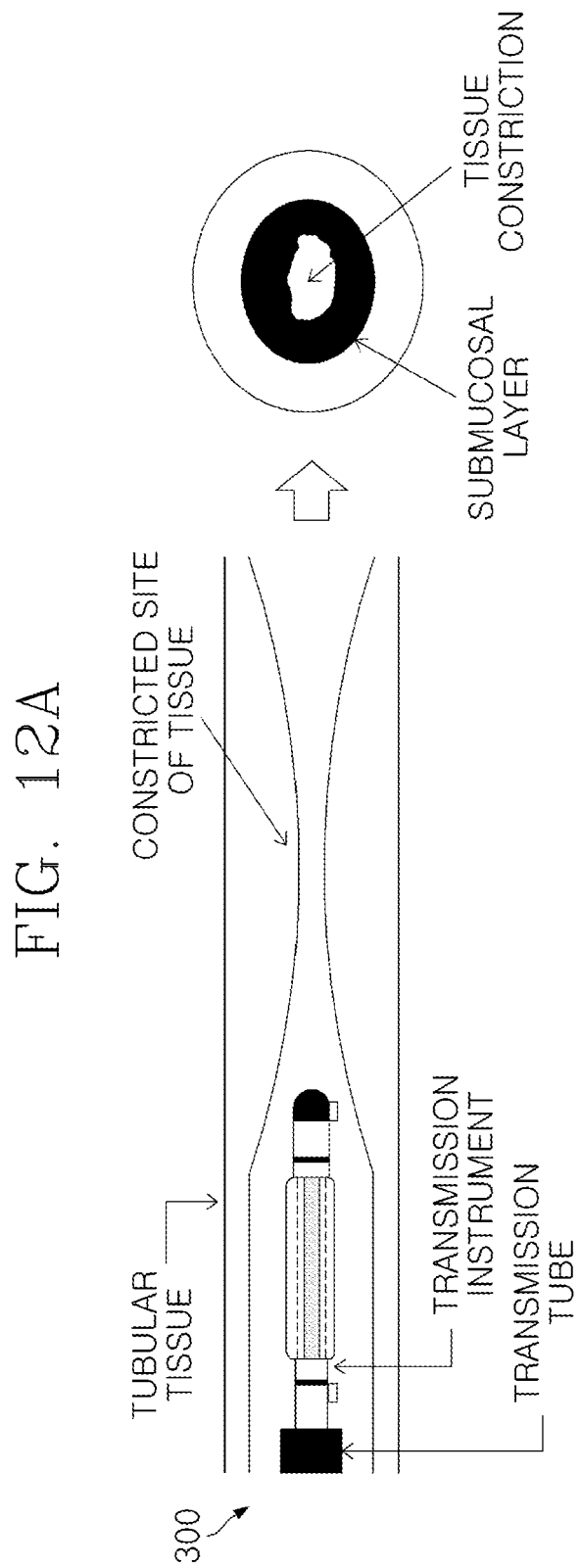

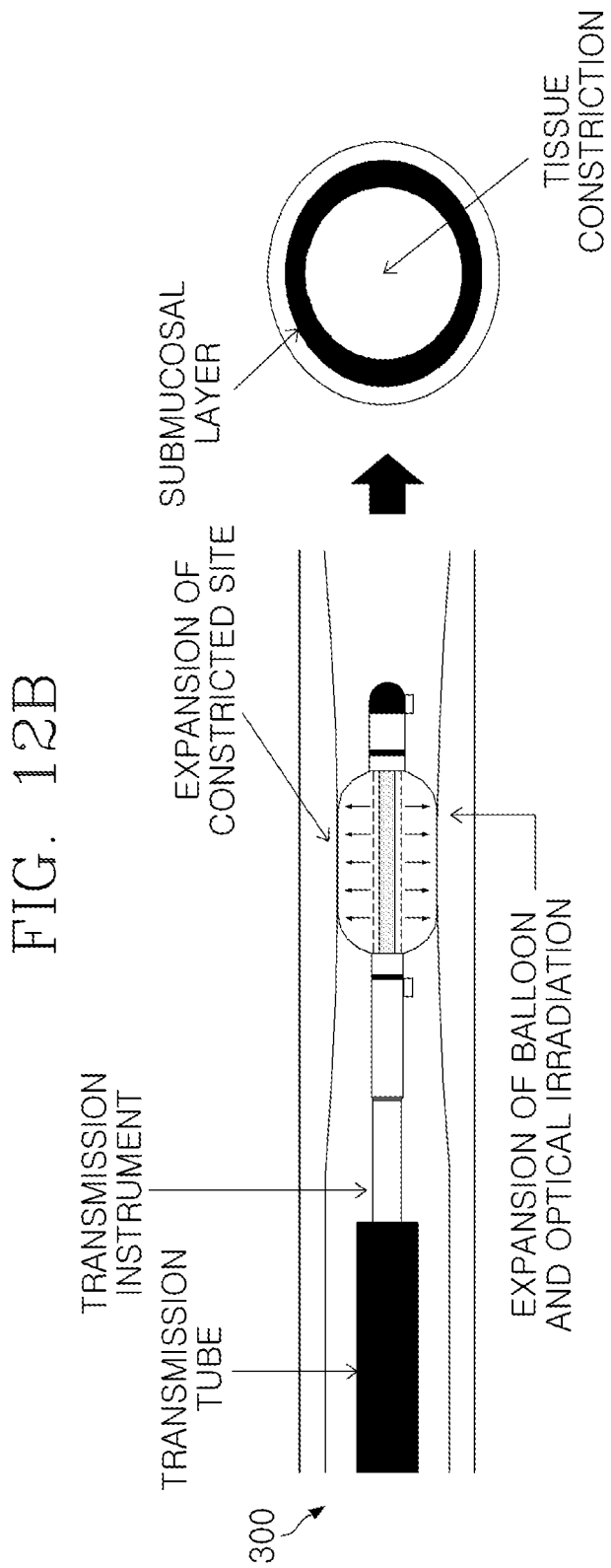

OPTICAL IRRADIATION APPARATUS

CROSS-REFERENCE TO RELATED APPLICATION

This application is a national stage application, filed under 35 U.S.C. § 371, of International Patent Application No. PCT/KR2018/013069, filed on Oct. 31, 2018, which claims the priority of Korean application No. 10-2018-0059045 filed on May 24, 2018, the contents of which are incorporated by reference.

TECHNICAL FIELD

The present invention relates to an optical irradiation apparatus, and more particularly, to an optical irradiation apparatus that transmits electromagnetic energy into an endoscope or a narrow channel.

BACKGROUND ART

Malignant gastrointestinal stenosis refers to a disease in which the lumen of the digestive system is narrowed due to various malignant diseases such as esophageal cancer, gastric cancer, and colorectal cancer, and obstruction of food passage occurs. Typically, a patient with the malignant gastrointestinal stenosis cannot swallow food and releases no bile, which can lead to severe weight loss, malnutrition, and jaundice, and in a serious case, the malignant gastrointestinal stenosis is a disease that causes a high risk of premature death.

In the case of a high-frequency thermotherapy and a photodynamic therapy for treating the above-mentioned diseases, a medical laser device in the related art generates rectilinear high-output energy, which causes a risk of perforation of the gastrointestinal tract and heat damage to the surrounding tissues and a risk of perforation, hemorrhage, and photosensitivity.

An optical irradiation apparatus in the related art treats only constricted tissue of the digestive system by using an optical fiber and contracting and expanding an entire catheter but has a problem in that it is impossible to expand the constricted tissue, and thus an efficient treatment cannot be performed.

Further, because the optical irradiation apparatus in the related art uses the optical fiber and emits optical energy only in a predetermined direction, the optical irradiation apparatus cannot emit energy toward particular tissue in various directions or at various angles.

Therefore, there is a gradually increasing need for an optical irradiation apparatus capable of effectively necrosing an entire tumor by three-dimensionally emitting constant energy.

DISCLOSURE

Technical Problem

An object of the present invention is to provide an optical irradiation apparatus capable of effectively necrosing an entire tumor by three-dimensionally emitting contact energy.

Technical Solution

To solve the technical problem, the present invention provides an optical irradiation apparatus including: a dual laser light source unit which simultaneously or selectively outputs multiple light sources created with different outputs; an optical fiber which is connected to the dual laser light source unit, receives the light outputted from the dual laser light source unit, and emits the received light through an embossed end surface; and an inflatable balloon catheter which is formed to surround the embossed end surface of the optical fiber and expands constricted tissue.

In addition, the optical irradiation apparatus may further include a light coupling unit that couples the multiple light sources created with the different outputs.

In addition, the multiple light sources may include a low-output light source created with an output of 10 mW to 5 W and a high-output light source created with an output of 1 W to 60 W.

In addition, the low-output light source may be a light source used to recuperate tissue or inhibit a relapse of injury.

In addition, the high-output light source may be a light source used for removal of tissue or coagulative necrosis.

In addition, the entire end surface of the optical fiber may be embossed so that the light is emitted through the entire embossed surface.

In addition, the end surface of the optical fiber may be embossed at predetermined intervals so that the light is emitted partially.

In addition, a portion of the end surface of the optical fiber, which corresponds to a predetermined angle in an axial direction, may be embossed so that the light is emitted at the predetermined angle in the axial direction.

In addition, a portion of the end surface of the optical fiber, which corresponds to a predetermined angle in an axial direction, may be embossed at predetermined intervals so that the light is emitted partially at the predetermined angle in the axial direction.

In addition, a shape of the inflatable balloon catheter may be any one of a quadrangular shape, a circular shape, an elliptical shape, a conical shape, a tapered shape, and a stepped shape.

In addition, a diameter of the inflatable balloon catheter may be 1 to 10 mm, and a length of the inflatable balloon catheter may be 5 to 25 mm.

In addition, a material of the inflatable balloon catheter may be any one of polytetrafluoroethylene (PTFE), polyethylene, polyvinyl chloride, nylon 66, nylon 11, nylon 12, urethane, polypropylene, polycarbonate, ABS, Pebax, polyether ether ketone (PEEK), and polyethylene terephthalate (PET).

In addition, a surface of the inflatable balloon catheter may be coated with medication.

In addition, the optical irradiation apparatus may further include a transmission tube having a first channel for receiving the optical fiber, a second channel for allowing a substance for expanding the inflatable balloon catheter to come into and out of the second channel, and a third channel for receiving a guide wire that ensures an entry route.

In addition, the first channel may be circular and the second channel may be semi-circular.

In addition, the third channel may be formed inside or outside the transmission tube.

In addition, the optical irradiation apparatus may further include a protective cap which is made of a transparent material and provided at an end of the optical fiber to protect the end of the optical fiber.

In addition, a surface of the inflatable balloon catheter may come into contact with constricted tissue and may expand to expand the constricted tissue, and the optical fiber may be positioned in the expanded inflatable balloon catheter and may emit the light in a state in which the optical fiber is not in contact with the constricted tissue.

Advantageous Effects

Effects of the optical irradiation apparatus according to the exemplary embodiments of the present invention will be described below.

With the optical irradiation apparatus according to the present invention, it is possible to effectively treat constricted tissue during a procedure of performing an anticancer therapy on all human bodies with various types of cancers, and it is possible to mitigate patient's pain by reducing a relapse rate of stenosis after the photothermal therapy.

In addition, it is possible to improve treatment efficiency by selectively emitting light by using a low-output light source, a high-output light source, or a combination thereof in accordance with the treatment purpose.

In addition, it is possible to accurately irradiate the constricted tissue with light by using the inflatable balloon catheter that expands the constricted tissue.

In addition, it is possible to irradiate a particular tissue with light in various directions or at various angles by means of the optical fiber having an end surface embossed in all directions or some directions.

However, the effects obtained by the optical irradiation apparatus according to the exemplary embodiments of the present invention are not limited to the aforementioned effects, and other effects, which are not mentioned above, will be clearly understood by those skilled in the art from the following description.

DESCRIPTION OF DRAWINGS

The accompanying drawings included as a part of the detailed description for helping understand the present invention provide exemplary embodiments of the present invention, and the technical spirit of the present invention will be described with reference to the detailed description.

FIGS. 12A and 12B are views illustrating an example in which the transmission instrument 300 according to the present invention is positioned at a constricted site and emits light.

BEST MODE

Figure 7:
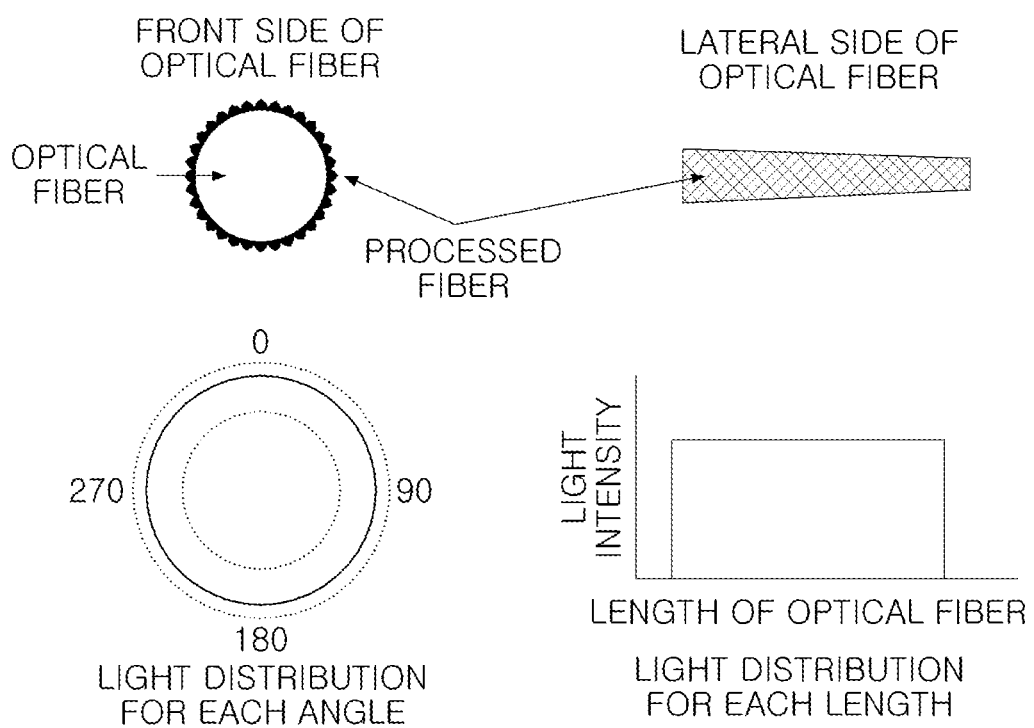
FIG. 7 is a view illustrating a shape of an optical fiber having an end surface that is entirely embossed.

FIG. 7 is a view illustrating a shape of an optical fiber having an end surface that is entirely embossed.

FIG. 7 is a view illustrating the optical fiber of which the entire surface is constantly embossed, and the optical fiber emits light radially over 360°. Since the entire surface of the optical fiber is entirely embossed constantly in the axial direction of the optical fiber, it is possible to constantly transmit light in the axial direction.

Figure 8:
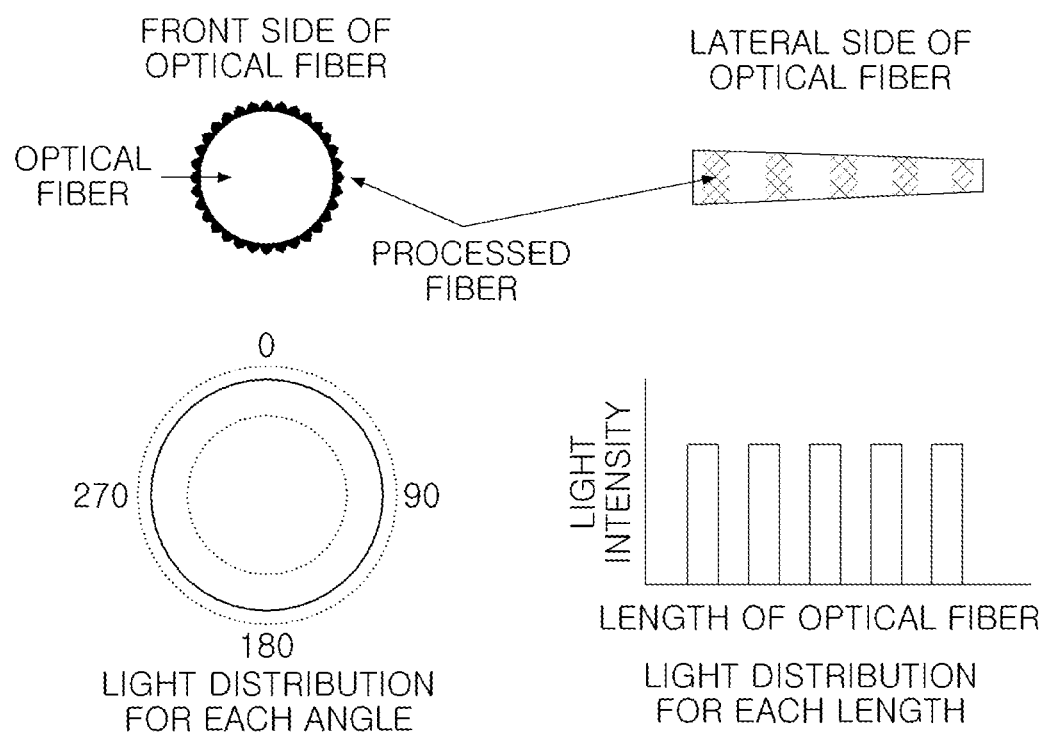
FIG. 8 is a view illustrating a shape of an optical fiber having an end surface that is entirely embossed at predetermined intervals.

FIG. 8 is a view illustrating a shape of an optical fiber having an end surface that is entirely embossed at predetermined intervals.

FIG. 8 is a view illustrating the optical fiber having the end surface that is embossed at predetermined intervals, and the optical fiber emits light partially.

As illustrated in FIG. 8, since the entire surface of the optical fiber is embossed at a constant interval, it is possible to emit light radially over 360°. Since the entire surface of the optical fiber is constantly embossed partially in the axial direction of the optical fiber, it is possible to partially transmit light in the axial direction.

As described above, since the surface of the optical fiber is partially embossed, it is possible to partially (like a zebra pattern) adjust a distribution of light emitted to the tissue surface and a distribution of temperatures.

Figure 9:
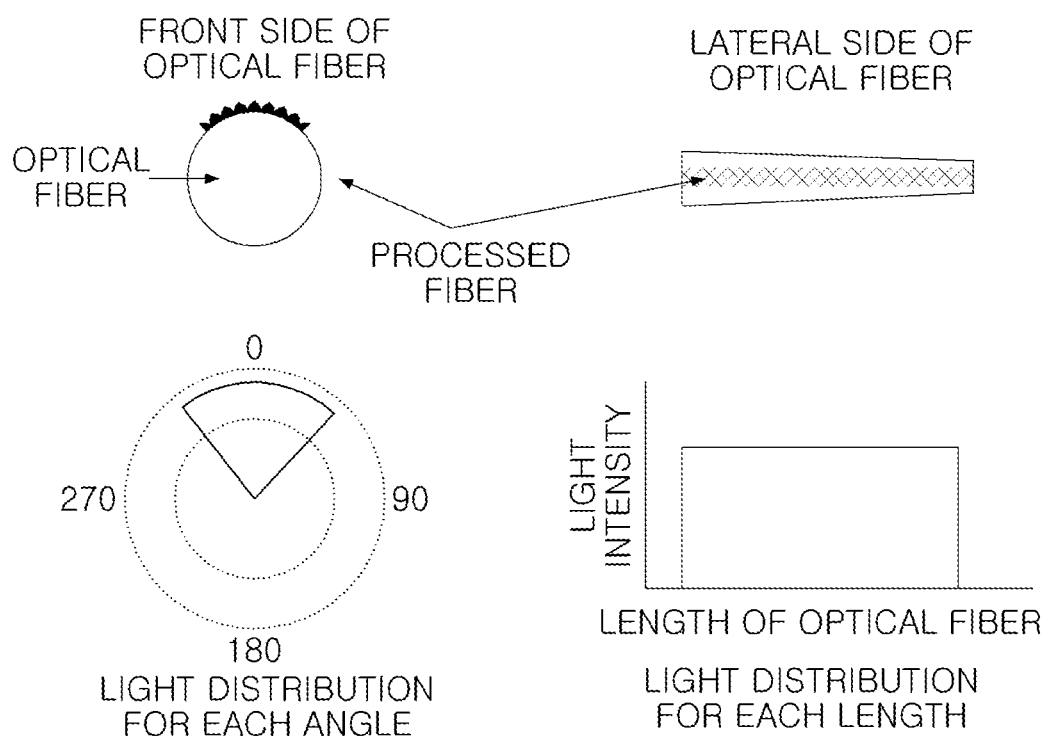
FIG. 9 is a view illustrating a shape of an optical fiber having an end surface of which the part corresponding to a predetermined angle in an axial direction is embossed.

FIG. 9 is a view illustrating a shape of an optical fiber having an end surface of which the part corresponding to a predetermined angle in an axial direction is embossed.

FIG. 9 is a view illustrating the optical fiber having the end surface of which the part corresponding to a predetermined angle in the axial direction is embossed, and the optical fiber may emit light in the axial direction at the predetermined angle. That is, the entire surface of the optical fiber is embossed only at a predetermined angle, such that light may be emitted radially (in a fan shape) and partially at a predetermined angle based on the axis.

As described above, since the entire surface of the optical fiber is constantly embossed partially only at a predetermined angle in the axial direction of the optical fiber, it is possible to constantly transmit light in the axial direction. Since the light may be emitted partially, it is possible to selectively perform the phototherapy on the constricted site when the constricted site is present at a part of tubular tissue.

Figure 10:
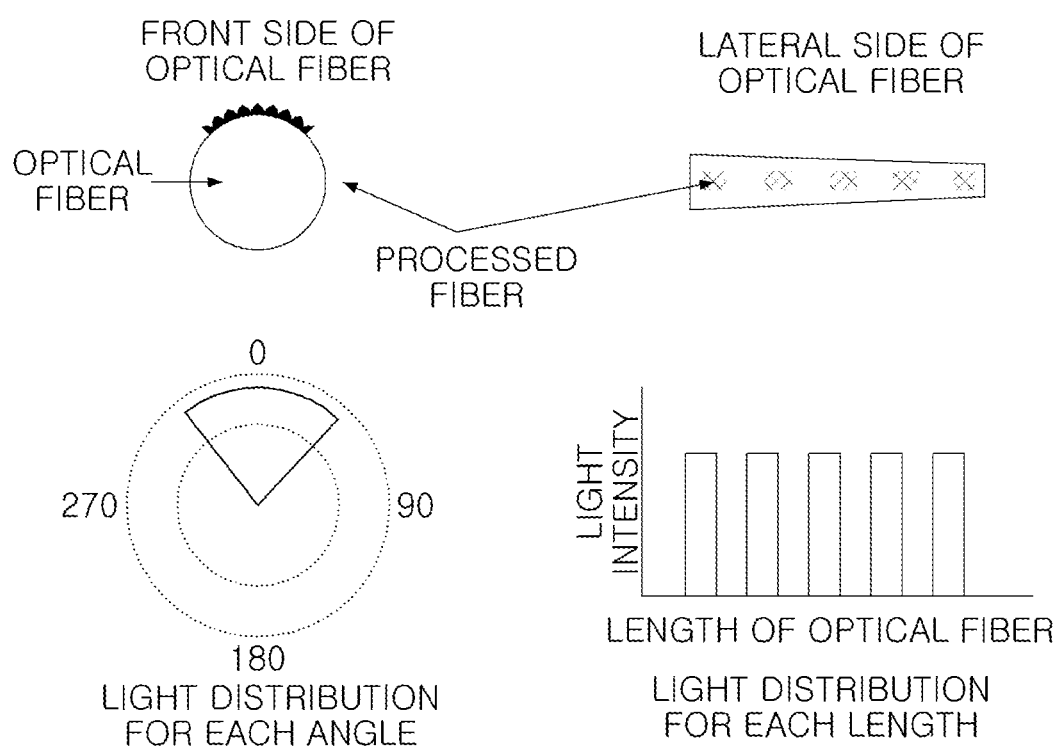
FIG. 10 is a view illustrating a shape of an optical fiber having an end surface of which the part corresponding to a predetermined angle in the axial direction is embossed at predetermined intervals.

FIG. 10 is a view illustrating a shape of an optical fiber having an end surface of which the part corresponding to a predetermined angle in the axial direction is embossed at predetermined intervals.

FIG. 10 is a view illustrating the optical fiber having the end surface of which the part corresponding to the predetermined angle along the circumference is embossed on the side of the end surface (side-embossed) forming side-embossed portions at predetermined intervals in the axial direction, and the optical fiber may emit light partially in the axial direction at the predetermined angle from each side-embossed portion. In this case, it is possible to partially emit light constantly in the axial direction.

Meanwhile, an optical output of visible rays to be transmitted to the tissue surface from the optical fiber may be 1 W to 60 W, and density of light to be transmitted may be 10 to 600 W/cm$^2$. For recuperation of the treated tubular constricted tissue and treatment of restenosis, an optical output of visible rays to be transmitted to the tissue surface from the optical fiber may be 10 mW to 5 W, and density of light to be transmitted may be 0.01 to 50 W/cm$^2$.

MODE FOR INVENTION

Terms or words used in the specification and the claims should not be interpreted as being limited to a general or dictionary meaning and should be interpreted as a meaning and a concept which conform to the technical spirit of the present invention based on a principle that an inventor can appropriately define a concept of a term in order to describe his/her own invention by the best method. Therefore, the exemplary embodiments disclosed in the present specification and the configurations illustrated in the drawings are just the best preferred exemplary embodiments of the present invention and do not represent all the technical spirit of the present invention. Accordingly, it should be appreciated that various equivalents and modified examples capable of substituting the exemplary embodiments may be made at the time of filing the present application. Hereinafter, the optical irradiation apparatus according to the exemplary embodiment of the present invention will be described in detail with reference to the accompanying drawings.

Figure 1:
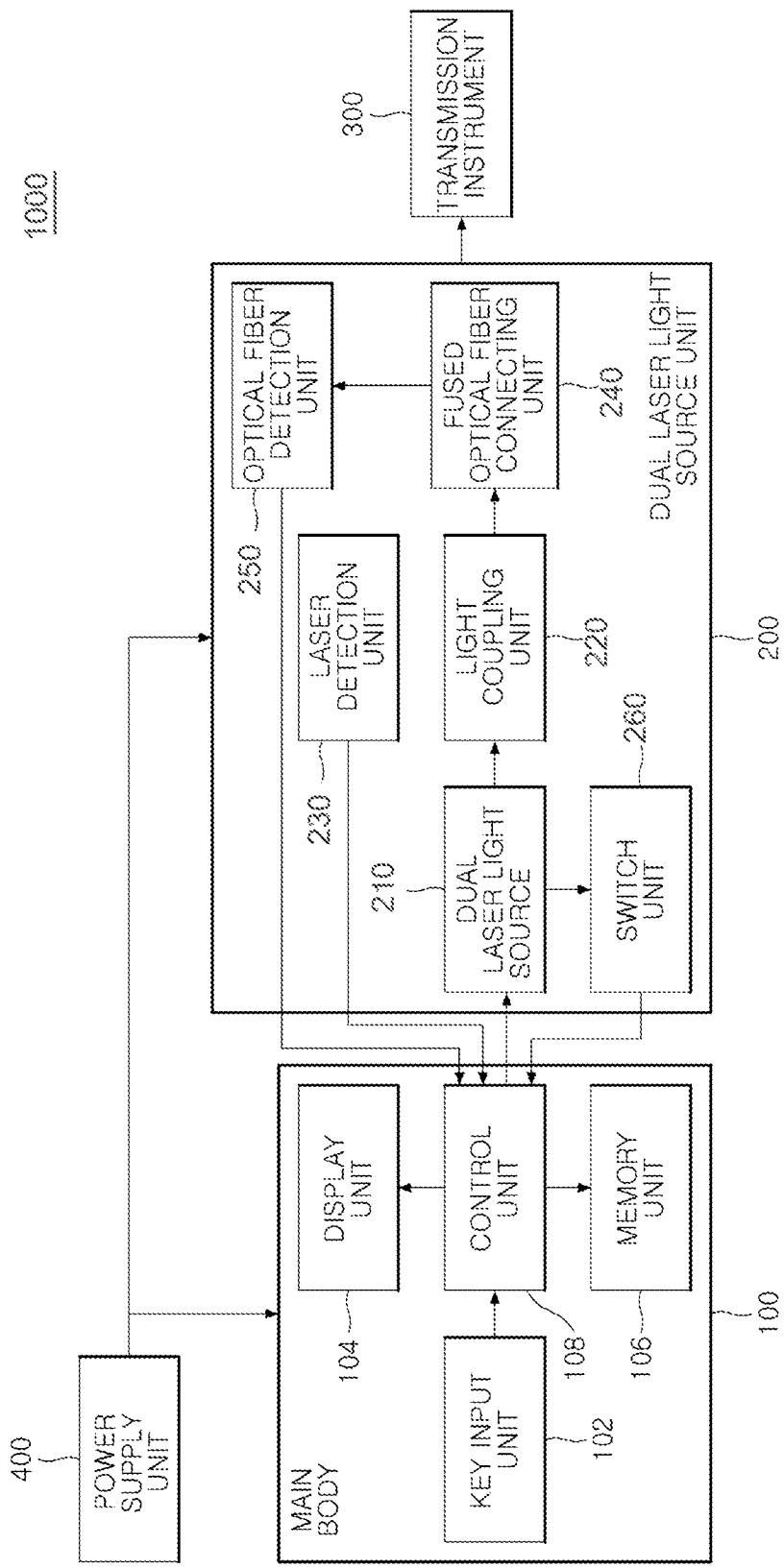
FIG. 1 is a block diagram illustrating an entire configuration of an optical irradiation apparatus 1000 according to the present invention.

FIG. 1 is a block diagram illustrating an entire configuration of an optical irradiation apparatus 1000 according to the present invention.

The optical irradiation apparatus 1000 according to the present invention is an optical irradiation apparatus that transmits light into an endoscope or a narrow channel through a light transmission instrument having an entirely or partially embossed end surface by using a dual laser light source, which may simultaneously or selectively combine multiple light sources using visible rays or infrared rays, and using an inflatable balloon catheter which expands constricted tissue.

The optical irradiation apparatus 1000 according to the present invention includes a main body 100, a dual laser light source unit 200, and a transmission instrument 300.

The main body 100 includes a key input unit 102 which has all selection buttons for operating and controlling the optical irradiation apparatus and receives desired driving modes from a user, a display unit 104 which displays the modes selectable by the user and displays an operating state, a memory unit 106 which stores a series of created information such as intensity of light, irradiation time, and an irradiation interval for each mode, and a control unit 108 which controls an overall operation of the optical irradiation apparatus and outputs a laser emission control signal so that light is emitted with the intensity, the irradiation time, and the irradiation interval which are designated based on a selected mode inputted from the key input unit.

The dual laser light source unit 200 includes a dual laser light source 210 which simultaneously or selectively outputs multiple light sources created with different outputs, a light coupling unit 220 which couples (or separate) the multiple light sources created with the different outputs, a laser detection unit 230 which automatically controls the laser outputs, a fused optical fiber connecting unit 240 which integrates the electromagnetic energy created by the transmission instrument into the optical fiber, an optical fiber detection unit 250 which checks for an optical fiber connection state and informs the display unit of the optical fiber connection state, and a switch unit 260 which controls an on/off operation of the optical irradiation.

Meanwhile, the optical irradiation apparatus 1000 according to the present invention includes the transmission instrument 300 which may transmit the created electromagnetic energy to an endoscope or a narrow channel, and a power supply unit 400 which supplies electric power to the main body 100 and the dual laser light source unit 200, and the dual laser light source unit 200 and the transmission instrument 300 will be described in detail with reference to the following drawings.

Figure 2:
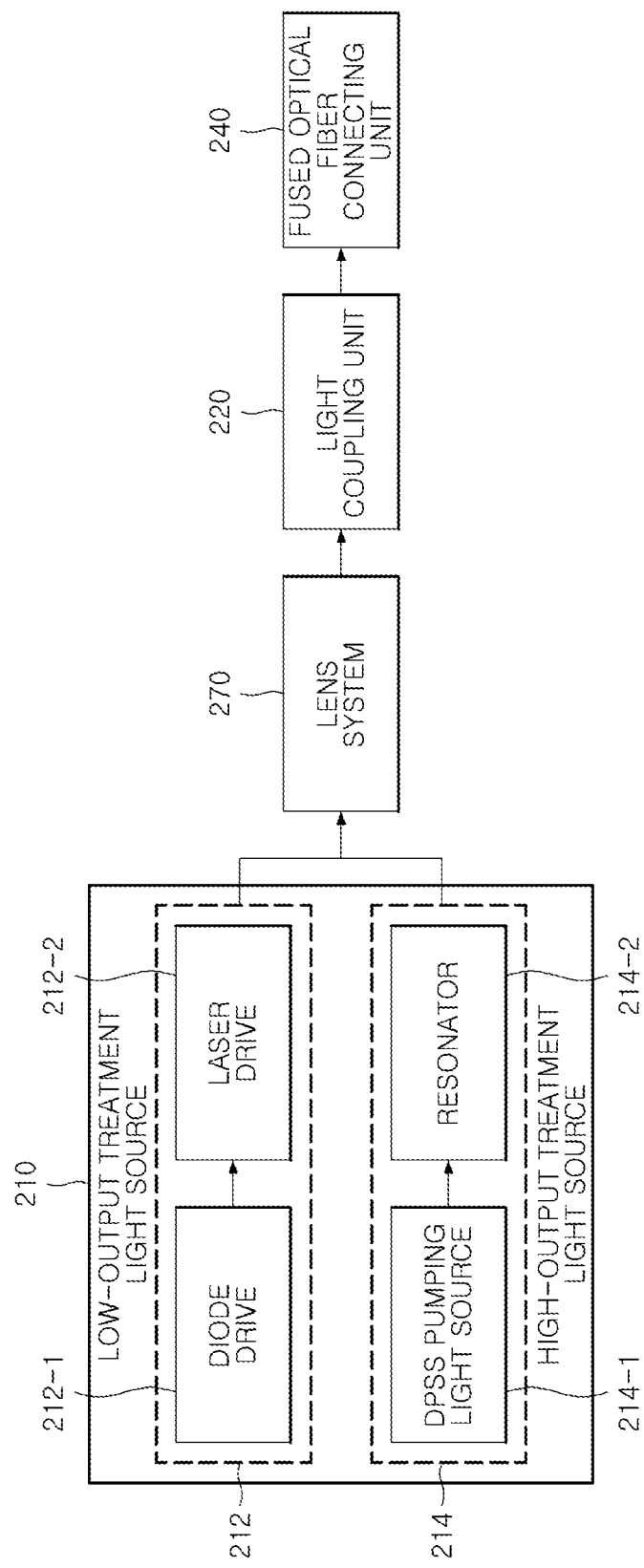
FIG. 2 is a block diagram illustrating a configuration of a dual laser light source unit 200 according to the present invention.

FIG. 2 is a block diagram illustrating a configuration of the dual laser light source unit 200 according to the present invention.

The dual laser light source 210 included in the dual laser light source unit 200 according to the present invention includes a low-output light source 212 and a high-output light source 214. That is, the laser light source unit, which creates multiple wavelengths, includes the low-output and high-output treatment light sources, couples the multiple wavelengths of the light sources 212 and 214 by using a lens system 270, integrates the multiple wavelengths into the optical fiber, and transmits energy.

The low-output light source 212 includes a diode drive 212-1 and a laser diode 212-2. The diode drive 212-1 may primarily receive a signal in respect to the selected mode from the control unit 108, and may drive the laser diode 212-2 based on the signal in accordance with the selected intensity, the selected irradiation time, and the selected irradiation interval, thereby creating light.

The high-output light source 214 includes a pumping light source 214-1 and a resonator 214-2. The light is pumped by the pumping light source 214-1, and high-output optical energy may be created by means of the resonator. A high-output diode pumped-solid state (DPSS) pumping light source, which outputs a high output of 1000 W or more, may be used as the pumping light source.

Specifically, the signal in respect to the selected mode is received first from the control unit 108, and the pumping light source 214-1 is driven in accordance with the selected intensity, the selected irradiation time, and the selected irradiation interval, such that a desired wavelength and optical energy may be created by means of the resonator 214-2. Here, a wavelength of the DPSS laser used for the pumping may be between 800 nm and 1040 nm. In addition to the DPSS light source, a diode laser, a frequency multiplied solid state laser, an ultraviolet/IR flash lamp, a light emitting diode LED, or an infrared bulb may be used as the high-output treatment light source.

Meanwhile, the low-output light source 212, which is used to recuperate the tissue or inhibit an injury relapse, may use a wavelength of 450 to 750 nm, and an output range of the light source output to be used may be 10 mW to 5 W. A method used to emit a low-output wavelength may be a continuous wave mode or a pulsed wave mode.

A pulse length used in the pulsed wave mode may be microsecond (μs) to millisecond (ms), and a repetition rate used in the pulsed wave mode may be 1 Hz to 1,000 Hz.

The high-output light source 214, which is used to remove tissue or induce coagulative necrosis may use a wavelength of 500 to 600 nm or 1,000 to 1,200 nm, and an output range of the light source to be used may be 1 to 60 W. A method used to emit a high-output wavelength may be the pulsed wave mode.

A pulse length used in the pulsed wave mode may be nanosecond (ns) to millisecond (ms), and a repetition rate used in the pulsed wave mode may be 0.1 kHz to 30 kHz.

Meanwhile, because a main component of the constricted tissue is protein such as collagen, the inside of the tubular tissue may be partially or entirely blocked by the constriction, and for this reason, the constriction may obstruct a movement and a supply of a digestive fluid or a body secretion along the tubular tissue. In this case, it is possible to entirely or partially remove or coagulatively necrose the blocked constricted site by using the laser, but because the treated constricted site may be reconstricted due to injury during a thermal treatment, a laser having an additional wavelength may be used to eliminate or reduce the reconstriction.

Figure 3:
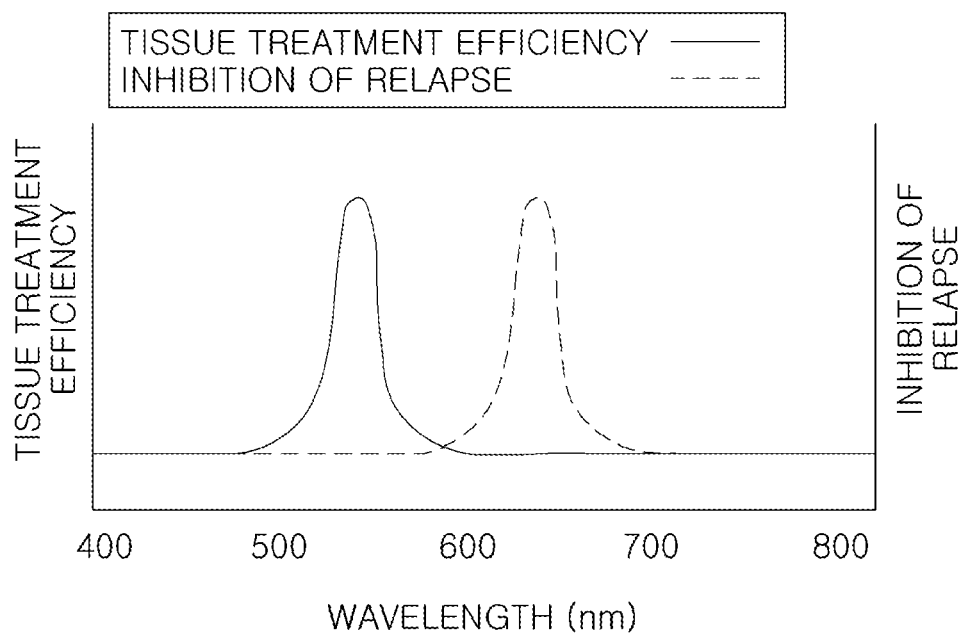
FIG. 3 is a graph illustrating an effect of treating tissue and an effect of inhibiting an injury relapse with respect to a wavelength of light emitted to treat the tissue.

FIG. 3 is a graph illustrating an effect of treating tissue and an effect of inhibiting an injury relapse with respect to a wavelength of light emitted to treat the tissue.

Referring to FIG. 3, it can be ascertained that the effect of treating tissue and the effect of inhibiting an injury relapse vary depending on the emitted wavelength. During the treatment of tissue, a relatively long wavelength in a visible ray region in the low-output light source may be used to promote recuperation of the treated site and inhibit a relapse of injury or stenosis. The wavelength used for the low-output light source hardly increases a temperature (within about 5 degrees).

In contrast, a relatively short wavelength in a visible ray region in the high-output light source may be used to induce a quick increase in temperature (60 to 120 degrees) through a light absorbing process of absorbers in the tissue and thus to improve tissue treatment efficiency.

To treat the constricted tissue by means of the endoscope or the narrow channel, conditions of the low-output and high-output light sources are set in advance, and the multiple wavelengths may be sequentially (the wavelength of the high-output light source is used and then the wavelength of the low-output light source is used) or simultaneously transmitted by using the connected optical fiber.

Because the low-output and the high-output optical energy, which are transmitted through the endoscope or the narrow channel, may damage the surrounding tissue, it is necessary to perform a process of adjusting in advance a size of the inside of the tissue, a constriction length, types of optical fiber, a size of a catheter, a distance between tissue, or the like in order to minimize the damage to the surrounding tissue.

Meanwhile, to couple the multiple wavelengths as described above, the multiple wavelengths are coupled by using a beam splitter of the light coupling unit 220 and integrated into the connected optical fiber by using the optical lens 270, such that the optical energy is transmitted.

Figure 4:
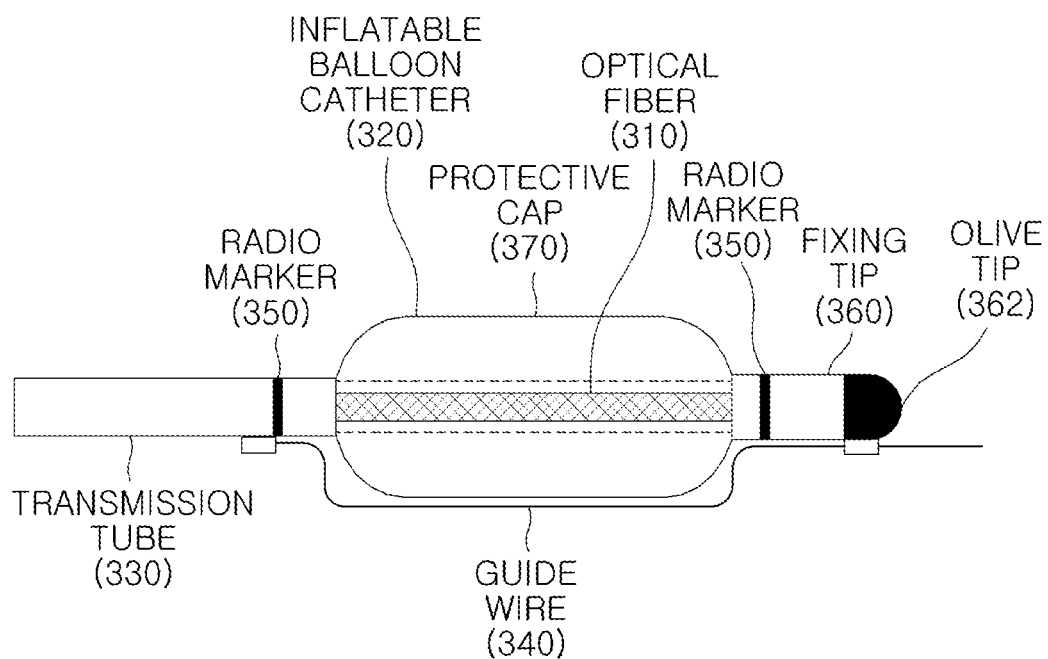
FIG. 4 is a block diagram illustrating a configuration of a transmission instrument 300 according to the present invention.

FIG. 4 is a view illustrating the transmission instrument 300 according to the exemplary embodiment of the present invention.

The transmission instrument 300 according to the present invention is configured to treat the tissue by means of the endoscope or the narrow channel, and includes an optical fiber 310, an inflatable balloon catheter 320, a transmission tube 330, a guide wire 340, radio markers 350, and a fixing tip 360.

The optical fiber 310 is connected through the fused optical fiber connecting unit 240 of the dual laser light source unit 200, receives light outputted from the dual laser light source unit 200, and emits the light received through an end surface.

The present invention uses the optical fiber 310 to transmit two types of wavelengths to the tissue to be treated, and a material of the optical fiber may be low/high OH silica, fused silica, germanium oxide, fluoride, phosphate, chalcogenide, or a hollow wave guide.

A configuration of the optical fiber 310 includes a core, a cladding, a buffer, and a jacket, and a diameter of the core of the optical fiber core may be 0.2 to 1 mm depending on density of energy to be transmitted, an overall diameter of the optical fiber may be 0.3 to 1.3 mm depending on an inner diameter of the endoscope, and an overall length of the optical fiber may be 1 to 4 m depending on a length of the endoscope. A length of an end portion of the optical fiber, where the optical irradiation is performed, may be 2 to 25 mm depending on the length the constricted tissue.

The end of the optical fiber is covered by a protective cap 370 to protect the end of the optical fiber 310, and the protective cap 370 may be made of transparent plastic, transparent acrylic, glass, quartz, PDMS, PTFE, or the like. A length of the protective cap at the end of the optical fiber may be 5 to 25 mm depending on a length of a laser irradiation site, and an outer diameter of the protective cap may be 1 to 5 mm.

When transmitting wavelengths of visible rays and infrared rays through the optical fiber 310, a light transmission ratio of the protective cap 370 is maintained between 60 and 95%, and the optical fiber 310 may be tapered to minimize transmission of light outputted from an entire surface of the end of the optical fiber 310.

The end surface of the optical fiber 310, which transmits optical energy, may be entirely or partially embossed to treat the constricted tissue positioned in the narrow tubular tissue, and the details thereof will be described below with reference to FIGS. 7 to 9.

The inflatable balloon catheter 320 may be coupled to an end of the transmission instrument 300 to constantly expand an internal structure of the constricted or narrowed tissue. The optical fiber 310 is positioned in the inflatable balloon catheter 320 to radially transmit the optical energy. That is, the inflatable balloon catheter 320 may be formed to surround the end surface of the optical fiber 310.

After the inflatable balloon catheter 320 expands, the optical fiber 310 positioned in the catheter is not in direct contact with the tissue during the optical irradiation, and the optical fiber is positioned at the center inside the tissue during the treatment. In this case, the optical fiber is positioned at the center inside the tissue to constantly treat the tubular tissue.

A diameter of the inflatable balloon catheter 320 for expanding the tissue may be 1 to 10 mm, and a length of the inflatable balloon catheter 320 may be 5 to 25 mm. A shape of the inflatable balloon may be quadrangular, circular, elliptical, conical, tapered, or stepped depending on a shape of the constricted tissue.

Figure 5:
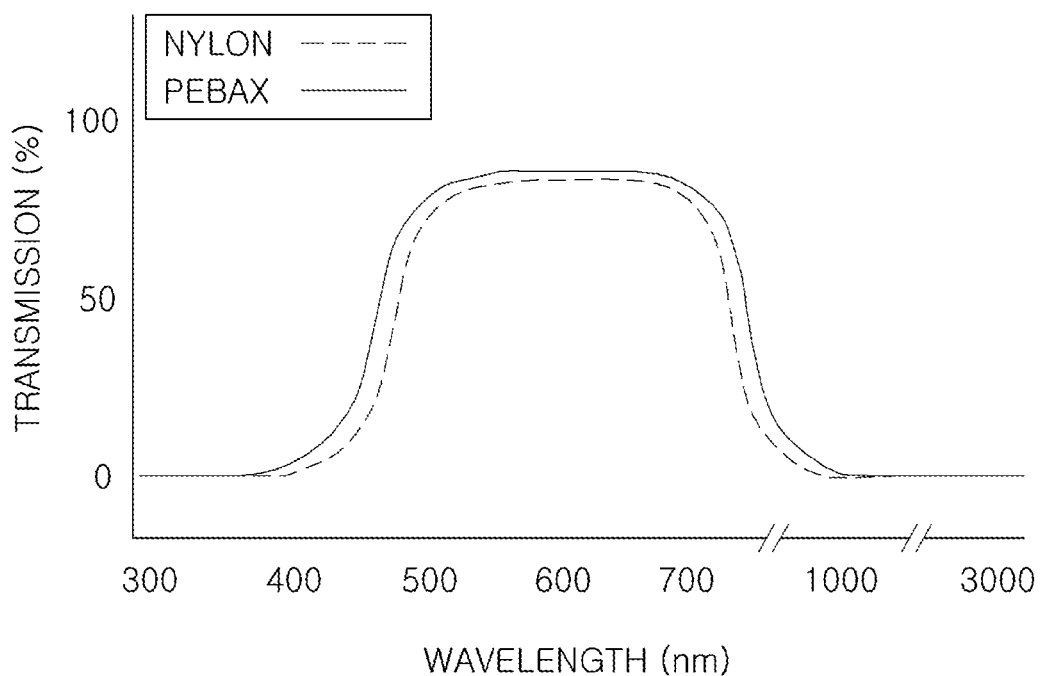
FIG. 5 is a graph illustrating transmittance in respect to substances of an inflatable balloon catheter 320 according to the present invention.

A substance, which constitutes the inflatable balloon catheter 320, may be polytetrafluoroethylene (PTFE), polyethylene, polyvinyl chloride, nylon 66, 11, 12, urethane, polypropylene, polycarbonate, ABS, Pebax, polyether ether ketone (PEEK), polyethylene terephthalate (PET), or the like. FIG. 5 is a graph illustrating transmittance in respect to substances of the inflatable balloon catheter. Referring to FIG. 5, it can be seen that the above-mentioned substance of the inflatable balloon catheter allows the wavelengths of the low-output and high-output visible rays to pass therethrough without a loss.

In addition, a surface of the inflatable balloon catheter 320 may be coated with medication, and the medication, together with the optical energy, may be delivered to the corresponding tissue during the optical irradiation, thereby improving a therapeutic effect. The deliverable medication may be mitomycin C, Indocyanine Green, Fucoidan, Phlorotannin, or Astaxanthin. The medication is injected into microparticles having a size of 5 to 350 µm, and the surface of the inflatable catheter may be coated with the medication.

Meanwhile, the radio markers 350 are positioned at front and rear sides of the end of the optical fiber 310, where light is emitted, to recognize an accurate position when inserting the transmission instrument 300 into the human body, such that it is possible to recognize the position of the transmission instrument with X-ray before the treatment.

Further, because the surface of the tissue surface may be injured or may have a hole when inserting the transmission instrument into a narrow tube, an olive tip 362 may be provided at the end of the transmission instrument to minimize the injury and the hole.

Air or a fluid (water, heavy water, a contrast agent, etc.) may be supplied into the inflatable balloon catheter 320 to expand the catheter. In this case, the air or fluid (water, heavy water, a contrast agent, etc.) to be supplied into the inflatable balloon catheter 320 may be selected to minimize absorption or scattering of the transmitted laser wavelength.

The transmission tube 330 is configured to insert the transmission instrument 300 into the endoscope or the narrow channel and serves to deliver the optical fiber 310, the inflatable balloon catheter 320, and the guide wire 340. The details of the transmission tube 330 will be described with reference to FIGS. 6A, 6B, and 6C.

The guide wire 340 is configured to ensure an entry route of the endoscope or the narrow channel and positioned inside or outside the transmission tube 330 to constitute a guide wire delivery channel.

An insertion route is ensured first by using the guide wire 340 before inserting the transmission instrument 300 into the tissue positioned in the tube through the endoscope or the narrow channel, and thereafter, the transmission instrument 300 is inserted into the endoscope or the narrow channel through the ensured insertion route so that the end of the optical fiber 310 may be positioned at the site to be treated.

A material of the guide wire 340 may be nitinol alloy or stainless steel, a diameter of the guide wire 340 may be 0.021 to 0.038 inches, and a length of the guide wire 340 may be 150 to 450 cm.

Figure 6A:
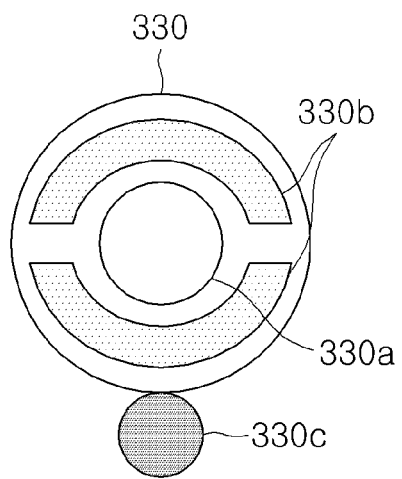
FIGS. 6A, 6B, and 6C are views illustrating one exemplary embodiment of a transmission tube 330 according to the present invention.
Figure 6B:
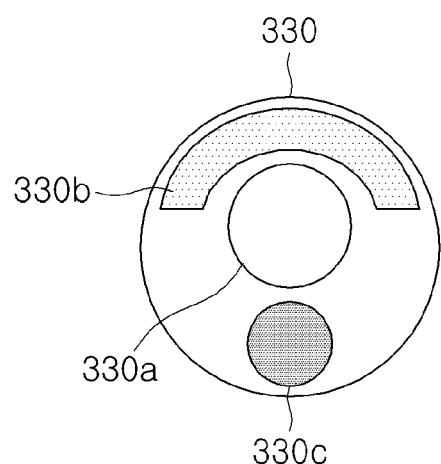
Figure 6C:
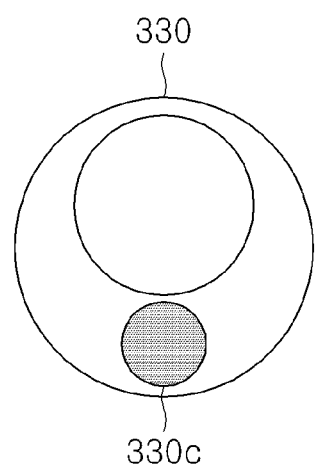

FIGS. 6A, 6B, and 6C are views illustrating one exemplary embodiment of the transmission tube 330 according to the present invention.

The transmission tube 330 may have a first channel 330a for receiving the optical fiber, a second channel 330b for allowing a substance for expanding the inflatable balloon catheter to come into and out of the second channel 330b, and a third channel 330c for receiving the guide wire that ensures the entry route.

That is, the transmission tube 330 enables the optical fiber 310 to be delivered to the center through the first channel 330a, enables air or a fluid for expanding the inflatable balloon catheter 320 to flow to the periphery of the center through the second channel 330b, and enables the guide wire to be delivered through the third channel 330c in a direction identical to a direction of the transmission tube.

Here, the first channel 330a may be circular, the second channel 330b may be semi-circular, and the third channel 330c may be formed inside or outside the transmission tube.

A diameter of the transmission tube 330 may be 0.5 to 5 mm depending on an inner diameter of the endoscope or the narrow channel. A channel of the transmission tube may have various shapes (the number of channels, the shape of the channel, etc.) for transmission to respective sites.

As illustrated in FIG. 6A, the first channel 330a for receiving the optical fiber has a circular shape, the second channel 330b for receiving the inflatable balloon catheter has two separated semi-circular shapes that may be positioned at upper and lower sides around the channel of the optical fiber, and the third channel 330c for receiving the guide wire may be formed outside the transmission tube 330.

As another exemplary embodiment, as illustrated in FIG. 6B, the first channel 330a is formed as a single channel, such that both of the second channel 330b and the third channel 330c may be formed inside the transmission tube 330.

As still another exemplary embodiment, as illustrated in FIG. 6C, each of the first channel 330a and the second channel 330b is configured as a single channel, and the third channel 330c may be formed inside the transmission tube 330.

Meanwhile, the transmission tube 330 may have a porous channel, and a substance, which constitutes the transmission tube 330, may be polytetrafluoroethylene (PTFE), polyethylene, polyvinyl chloride, nylon 66, 11, 12, urethane, polypropylene, polycarbonate, ABS, Pebax, polyether ether ketone (PEEK), polyethylene terephthalate (PET), or the like.

FIG. 7 is a view illustrating a shape of an optical fiber having an end surface that is entirely embossed.

FIG. 7 is a view illustrating the optical fiber of which the entire surface is constantly embossed, and the optical fiber emits light radially over 360°. Since the entire surface of the optical fiber is entirely embossed constantly in the axial direction of the optical fiber, it is possible to constantly transmit light in the axial direction.

FIG. 8 is a view illustrating a shape of an optical fiber having an end surface that is entirely embossed at predetermined intervals.

FIG. 8 is a view illustrating the optical fiber having the end surface that is embossed at predetermined intervals, and the optical fiber emits light partially.

As illustrated in FIG. 8, since the entire surface of the optical fiber is embossed at a constant interval, it is possible to emit light radially over 360°. Since the entire surface of the optical fiber is constantly embossed partially in the axial direction of the optical fiber, it is possible to partially transmit light in the axial direction.

As described above, since the surface of the optical fiber is partially embossed, it is possible to partially (like a zebra pattern) adjust a distribution of light emitted to the tissue surface and a distribution of temperatures.

FIG. 9 is a view illustrating a shape of an optical fiber having an end surface of which the part corresponding to a predetermined angle in an axial direction is embossed.

FIG. 9 is a view illustrating the optical fiber having the end surface of which the part corresponding to a predetermined angle in the axial direction is embossed, and the optical fiber may emit light in the axial direction at the predetermined angle. That is, the entire surface of the optical fiber is embossed only at a predetermined angle, such that light may be emitted radially (in a fan shape) and partially at a predetermined angle based on the axis.

As described above, since the entire surface of the optical fiber is constantly embossed partially only at a predetermined angle in the axial direction of the optical fiber, it is possible to constantly transmit light in the axial direction. Since the light may be emitted partially, it is possible to selectively perform the phototherapy on the constricted site when the constricted site is present at a part of tubular tissue.

FIG. 10 is a view illustrating a shape of an optical fiber having an end surface of which the part corresponding to a predetermined angle in the axial direction is embossed at predetermined intervals.

FIG. 10 is a view illustrating the optical fiber having the end surface of which the part corresponding to the predetermined angle in the axial direction is embossed at predetermined intervals, and the optical fiber may emit light partially in the axial direction at the predetermined angle. In this case, it is possible to partially emit light constantly in the axial direction.

Meanwhile, an optical output of visible rays to be transmitted to the tissue surface from the optical fiber may be 1 W to 60 W, and density of light to be transmitted may be 10 to 600 W/cm$^2$. For recuperation of the treated tubular constricted tissue and treatment of restenosis, an optical output of visible rays to be transmitted to the tissue surface from the optical fiber may be 10 mW to 5 W, and density of light to be transmitted may be 0.01 to 50 W/cm$^2$.

Figure 11:
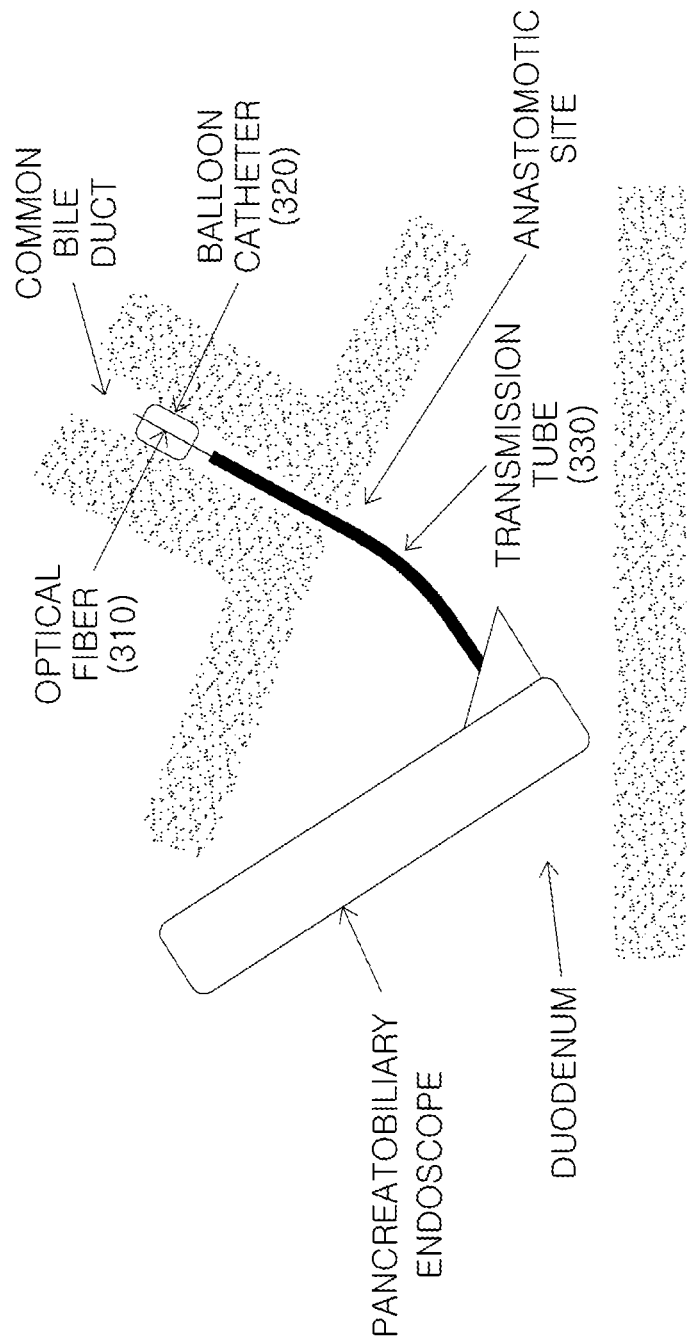
FIG. 11 is a view illustrating an example in which the optical irradiation apparatus 1000 according to the present invention is inserted into an anastomotic site.

FIG. 11 is a view illustrating an example in which the optical irradiation apparatus 1000 according to the present invention is inserted into an anastomotic site.

FIG. 11 is a view illustrating an example in which the guide wire is inserted into the anastomotic site by using the endoscope to ensure a route to a common bile duct, the transmission instrument is inserted along the guide wire through the endoscope to position the end of the transmission instrument at the constricted site, the tissue is expanded by the inflatable catheter, and light for treatment is emitted.

The surface of the inflatable balloon catheter comes into contact with the constricted tissue and expands to expand the constricted tissue, and the optical fiber is positioned inside the expanded inflatable balloon catheter and emits light in a state in which the optical fiber is not in contact with the constricted tissue. That is, with the inflatable catheter, the optical fiber is not in contact with the tissue and positioned at the center of the tubular tissue while the light is transmitted.

When the phototherapy is completed, the expanded catheter is contracted first, the guide wire and the transmission instrument are removed through the endoscope, and then the endoscope is withdrawn from the inside of the human body.

FIGS. 12A and 12B are views illustrating an example in which the transmission instrument 300 according to the present invention is positioned at the constricted site and emits light.

The inflatable balloon catheter is expanded when the transmission instrument 300 according to the present invention is inserted into the tubular tissue through the endoscope and the end of the transmission instrument 300 is positioned at the constricted site. After the inflatable balloon catheter is expanded, the laser light is radially transmitted from the optical fiber, and the optical fiber is always positioned at the center inside the inflatable balloon catheter in a state in which the optical fiber is not in contact with the tissue.

It can be seen that FIG. 12A illustrates that the constricted site of the tissue is blocked before the transmission instrument 300 is positioned, but FIG. 12B illustrates that the inside of the tissue is expanded as the catheter expands, and the optical irradiation is enabled by maintaining the expanded part.

Figure 13:
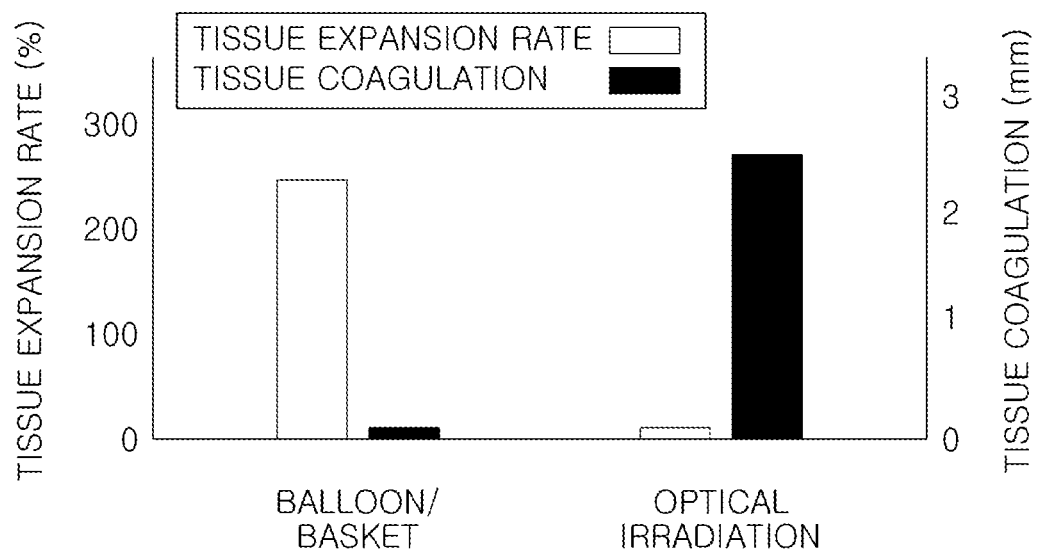
FIG. 13 is a graph illustrating degrees of expansion and coagulation of tissue in accordance with the use of the optical irradiation apparatus 1000 according to the present invention.

FIG. 13 is a graph illustrating degrees of expansion and coagulation of tissue in accordance with the use of the optical irradiation apparatus 1000 according to the present invention.

It is ascertained that when the optical irradiation apparatus 1000 is inserted into the constricted site of the tissue and the tissue is expanded by using the inflatable balloon, an internal area is expanded by two or more times an initially constricted area.

Meanwhile, coagulative necrosis having a predetermined thickness may be radially generated when treating the constricted tissue through the optical irradiation, but it is ascertained that when the expanded tissue is irradiated with light by the optical irradiation apparatus 1000 according to the present invention, the coagulation inside the tubular tissue is 3 mm or less.

While the present invention has been described in detail above with reference to the representative exemplary embodiments, those skilled in the art to which the present invention pertains will understand that the exemplary embodiment may be variously modified without departing from the scope of the present invention. Therefore, the scope of the present invention should not be limited to the described exemplary embodiments, and should be defined by not only the claims to be described below, but also those equivalent to the claims.

The invention claimed is:

1. An optical irradiation apparatus comprising:
   a light source unit which simultaneously or selectively outputs multiple laser light sources;
   a light coupling unit coupling the multiple laser light sources;
   a fused optical fiber connector configured to integrate outputs from each of the multiple laser light sources that the light coupling unit is coupled to as a light to be emitted through an optical fiber;
   the optical fiber emitting the light from the fused optical fiber connector through an end surface that is embossed;
   an inflatable balloon catheter which is formed to surround the end surface of the optical fiber and is configured to expand constricted tissue;
   a first radio marker positioned at a front side of the inflatable balloon catheter;
   a second radio marker positioned at a rear side of the inflatable balloon catheter; and
   a transmission tube having a first channel for receiving the optical fiber, a second channel for allowing a substance for expanding the inflatable balloon catheter to come into and out of the second channel, and a third channel for receiving a guide wire that ensures an entry route, wherein the third channel is formed inside the transmission tube,
   wherein the first channel is circular and positioned at the center of the transmission tube, and the second channel is semi-circular and positioned at the periphery of the center,
   wherein the end surface of the optical fiber includes a plurality of side-embossed portions, side-embossed at predetermined intervals in an axial direction and at a predetermined angle along a circumference of the optical fiber so that the light is emitted from each side-embossed portion at the predetermined intervals in the axial direction and at the predetermined angle along the circumference to form partially a radial fan shape from a center point of the optical fiber at the predetermined interval, and wherein the optical irradiation apparatus is for treating a tubular tissue of a human body's digestive system, wherein the first and second radio markers recognize a position when being inserted into the human body before treatment with X-ray, wherein the multiple laser light sources include a low-output light source created with an output of 10 mW to 5 W and a high-output light source created with an output of 1 W to 60 W, wherein the low-output light source is a light source used to recuperate tissue or inhibit a relapse of injury, and the high-output light source is a light source used for removal of tissue or coagulative necrosis, and wherein a material of the inflatable balloon catheter is any one of polytetrafluoroethylene (PTFE), polyethylene, polyvinyl chloride, nylon 66, nylon 11, nylon 12, urethane, polypropylene, polycarbonate, ABS, Pebax, polyether ether ketone (PEEK), and polyethylene terephthalate (PET).

2. The optical irradiation apparatus of claim 1, wherein a shape of the inflatable balloon catheter is any one of a quadrangular shape, a circular shape, an elliptical shape, a conical shape, a tapered shape, and a stepped shape.

3. The optical irradiation apparatus of claim 1, wherein a diameter of the inflatable balloon catheter is in a range of 1 to 10 mm, and a length of the inflatable balloon catheter is in a range of 5 to 25 mm.

4. The optical irradiation apparatus of claim 1, wherein a surface of the inflatable balloon catheter is coated with a medication.

5. The optical irradiation apparatus of claim 1, further comprising:

a protective cap which is made of a transparent material and provided at an end of the optical fiber to protect the end of the optical fiber.

6. The optical irradiation apparatus of claim 1, wherein a surface of the inflatable balloon catheter is configured to come into contact with the constricted tissue and expands to expand the constricted tissue, and the optical fiber is positioned in the expanded inflatable balloon catheter and emits the light in a state in which the optical fiber is not in contact with the constricted tissue.

* * * * *